ns Patent [19]

Umezawa et al.

[11] 4,357,466
[45] Nov. 2, 1982

[54] PROCESSES FOR THE PRODUCTION OF 3'-DEOXYKANAMYCIN A AND INTERMEDIATES

[75] Inventors: Hamao Umezawa; Sumio Umezawa, both of Tokyo; Tsutomu Tsuchiya, Yokohama; Tomo Jikihara, Kawasaki, all of Japan

[73] Assignee: Zaidan Hojin Biseibutsu Kagaku Kenkyu Kai, Tokyo, Japan

[21] Appl. No.: 198,612

[22] Filed: Oct. 20, 1980

[30] Foreign Application Priority Data

Oct. 31, 1979 [JP] Japan .................................. 54-139798

[51] Int. Cl.³ ...................... A61K 31/71; C07H 15/22
[52] U.S. Cl. .................................. 536/13.8; 424/180; 536/13.7
[58] Field of Search ......................................... 536/10

[56] References Cited

U.S. PATENT DOCUMENTS 3,753,973  8/1973  Umezawa et al. .................... 536/10
4,170,641 10/1979  Akita et al. .......................... 536/10
4,195,170  3/1980  Umezawa et al. .................... 536/10

Primary Examiner—Johnnie R. Brown
Attorney, Agent, or Firm—Larson and Taylor

[57] ABSTRACT

3'-Deoxykanamycin A useful as antibacterial agent is produced from a protected kanamycin A derivative either by a process comprising imidazolylthiocarbonylation of the 3'- and 2''-hydroxyl groups of 4'',6''-O-cyclohexylidene-4'-O:6'-N-carbonyl-5,2'-O-isopropylidene-1,3,3''-tri-N-tosylkanamycin A, preferential removal of the 3'-imidazolylthiocarbonyloxy group with tributyltin hydride for the 3'-deoxygenation, followed by removal of the 2''-O-imidazolylthiocarbonyl group with aqueous ammonia, removal of the N-tosyl groups with alkali or alkaline earth metal in liquid ammonia, hydrolytic fission of the 4',6'-cyclic carbamate ring and concurrent removal of the 5,2'-O-isopropylidene group and 4'',6''-O-cyclohexylidene group, or by a process comprising selective acetylation of the 2''-hydroxyl group of said protected kanamycin A derivative with acetyl chloride in pyridine, trifluoromethanesulfonylation of the 3'-hydroxyl group, followed by concurrent removal of the 3'-trifluoromethanesulfonyloxy group and N-tosyl groups with alkali metal in liquid ammonia, removal of the 2''-O-acetyl group concurrently with hydrolytic fission of 4',6'-cyclic carbamate, and hydrolytic removal of the 5,2'-O-isopropylidene and 4'',6''-O-cyclohexylidene groups.

5 Claims, No Drawings

PROCESSES FOR THE PRODUCTION OF 3'-DEOXYKANAMYCIN A AND INTERMEDIATES

SUMMARY OF THE INVENTION

This invention relates to new processes for the production of 3'-deoxykanamycin A which is useful as an antibacterial agent.

3'-Deoxykanamycin A is a substance active against bacteria resistant to kanamycin A as described in Japanese Patent Publication No. 33,109/76 or U.S. Pat. No. 3,929,761. The 1-N-α-hydroxy-ω-aminoacylated derivative of 3'-deoxykanamycin A has improved antibacterial activity against kanamycin A-resistant bacteria (see Japanese Patent Application Pre-publication "Kokai" No. 127,045/76 or U.S. Pat. No. 4,104,372). In particular, a derivative of 3'-deoxykanamycin A in which the 1-amino group has been acylated with a (S)-4-amino-2-hydroxybutyryl group, that is, 3'-deoxyamikacin, exhibits a higher antibacterial activity against any of the kanamycin-resistant bacteria, as compared to amikacin, that is, 1-N-[(S)-4-amino-2-hydroxybutyryl]-kanamycin A. The production of 3'-deoxyamikacin requires the preliminary preparation of 3'-deoxykanamycin A. In the past, however, 3'-deoxykanamycin A can be produced only by an inefficient method of said U.S. Pat. No. 3,929,761 or Japanese Patent Publication No. 33109/76 in which 6-azido-2,4-di-O-benzyl-3,6-dideoxy-α-D-ribohexopyranosyl chloride is condensed with 6-O-(2-O-benzyl-3-deoxy-3-ethoxycarbonylamino-4,6-O-isopropylidene)-N,N'-diethoxycarbonyl-2-deoxystreptamine and the resulting condensation product is treated for removing therefrom the amino-protecting groups and the hydroxyl-protecting groups to produce 3'-deoxykanamycin A. Accordingly, there has been a demand that 3'-deoxykanamycin A should be synthetized directly from kanamycin A. This demand is now met by this invention.

One the other hand, we, the present inventors, already developed a method for 3'-deoxygenation of neamine, kanamycin B and ribostamycin (see U.S. Pat. No. 3,929,762). The method of this U.S. patent, however, is not applicable to kanamycin A for 3'-deoxygenation of it. The method of U.S. Pat. No. 3,929,762 comprises a step where the 3'-hydroxyl group of neamine, kanamycin B or ribostamycin is selectively alkyl-, aryl- or aralkylsulfonylated with all the amino groups as well as the 4''- and 6''-hydroxy groups of these antibiotics having been protected by known protective groups. If kanamycin A which contains a 2'-hydroxyl group adjacent to the 3'-hydroxyl group in the molecule is subjected to the sulfonylation step of the method of the above U.S. patent, the 2'-hydroxyl group can be sulfonylated with the consequence that 2'-deoxygenation takes place inevitably and 3'-deoxykanamycin cannot be obtained as desired. In addition, in the past, it was not possible to develop a procedure by which the 2'-hydroxyl group of kanamycin A can be protected selectively so that the 2'-hydroxyl group is prevented from being sulfonylated.

We already succeeded in synthesizing 3',4'-dideoxykanamycin B from kanamycin B (Japanese Patent Publication Nos. 7579/75 and 46110/76; U.S. Pat. No. 3,753,973), and we have conducted research concerning synthesis of 3',4'-dideoxykanamycin A from kanamycin A (see our pending Japanese Patent Application No. 11402/79; copending U.S. patent application Ser. No. 114,779, now abandoned, filed 1-23, 80, now Pat. No. 4,298,727; U.K. Patent Application No. 8003417; Belgian Pat. No. 881,251 registered on Feb. 15, 1980). In this research, we have found that when kanamycin A is merely subjected to the method of deoxygenation comprising 3',4'-di-O-sulfonylation and subsequent treatment of the resulting 3',4'-di-O-sulfonic acid ester with sodium iodide and zinc power, which was successfully applicable in the semisynthesis of 3',4'-dideoxykanamycin B, there cannot be obtained 3',4'-dideoxykanamycin A as expected. This is because the kanamycin A molecule contains a 2'-hydroxyl group adjacent to the 3'-hydroxyl group thereof so that this 2'-hydroxyl group is sulfonylated concurrently with the sulfonylation of the 3'- and 4'-hydroxyl groups, with a consequence that the 2'-hydroxyl group once sulfonylated is removed at the same time that the removal of the sulfonylated 3'- and 4'-hydroxyl groups is performed by treating with sodium iodide and zinc powder.

In the research for synthesis of 3',4'-dideoxykanamycin A from kanamycin A, we have further found that 3',4'-dideoxykanamycin A cannot be synthesized from kanamycin A by applying thereto the same deoxygenation method as the one which was adopted in the synthesis of 3',4'-dideoxykanamycin B from kanamycin B, unless we are not able to prepare and provide such a protected kanamycin A derivative which is to be subjected to the procedure of de-oxygenation as mentioned above and of which the 3'- and 4'-hydroxyl groups of kanamycin A remain in the unprotected state, while the neighboring 2'-hydroxyl groups as well as all the other hydroxyl groups and all the amino groups exist in the protected or blocked state. However, no great difference is observed between the 2'-, 3'- and 4'-hydroxyl groups of kanamycin A in respect of their reactivity, and hence it was very difficult to find out any procedure by which the 2'-hydroxyl group can be protected while retaining the 3'- and 4'-hydroxyl groups unblocked.

We researched extensively in an attempt to provide such suitable kanamcyin A derivative. As a result, we have found that such a protected derivative of kanamycin A having 3'- and 4'-hydroxyl groups unblocked, having a protected or unprotected 2''-hydroxyl group and having the 2'-hydroxyl group as well as all the amino groups blocked may be prepared by means of a combination of an ingenious choice of the nature of the hydroxyl-protecting and amino-protecting groups employed, with an elaborate arrangement of the sequence of the respective stages of protecting each amino group and each hydroxyl group, in such a way that the 6'-amino group of kanamycin A which is the most reactive among the four amino groups of kanamycin A is at first blocked by an alkoxycarbonyl group, an aralkyloxycarbonyl group, especially a benzyloxycarbonyl group or an aryloxycarbonyl group known as one of the conventional amino-protecting groups; the 1-, 3- and 3''-amino groups of kanamycin A are then protected by an alkylsulfonyl group, an arylsulfonyl group or an aralkylsulfonyl group; the 4''- and 6''-hydroxyl group are simultaneously blocked by introducing a cyclohexylidene group therebetween; the free 4'-hydroxyl group and the alkoxycarbonylated, aralkyloxycarbonylated or aryloxycarbonylated 6'-amino group are subsequently condensed with each other into the form of a cyclic carbamate by treating with an alkali metal hydride, e.g. sodium hydride, resulting in simultaneous protection of the 4'-hydroxyl and 6'-amino groups; a pair of the 5-hydroxyl groups and 2'-hydroxyl groups are selectively and simultaneously blocked by introducing and bridging therebetween with a known divalent hydroxyl-protecting group such as an alkylidene group, especially an isopropylidene group, cyclohexylidene group, benzylidene group or tetrahydro-4-pyranylidene group; the 4',6'-carbamate ring once formed is ring-fissioned by treatment with an alkali to regenerate the free 4'-hydroxyl group and the free 6'-amino group; and finally the free 6'-amino group is blocked with an alkoxycarbonyl or aralkyloxycarbonyl group or an alkanoyl group such as acetyl. In this way, we succeeded in preparing a desired, suitably protected derivative of kanamycin A, and as a consequence, we succeeded in providing a route by which semi-synthesis of 3',4'-dideoxykanamycin A is achieved.

In the course of developing the process for the synthesis of 3',4'-dideoxykanamycin A, we have prepared a protected kanamycin A derivative of the formula

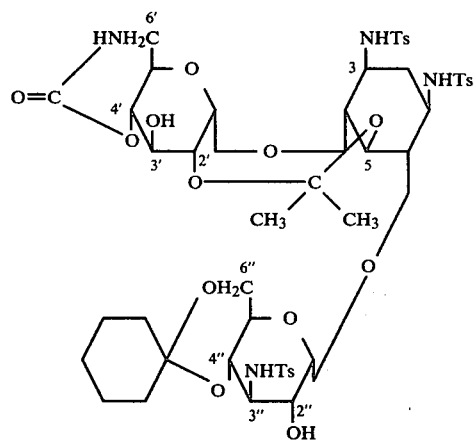

(I)

which is 4",6"-O-cyclohexylidene-4'-0:6'-N-carbonyl-5,2'-O-iso-propylidene-1,3,3"-tri-N-tosylkanamycin A (see Example 1 of our pending Japanese Patent Application No. 11402/79; U.S. patent application Ser. No. 114,779 and U.K. Patent Application No. 8003417).

DETAILED DESCRIPTION OF THE INVENTION

We have now succeeded in producing 3'-deoxykanamycin A semi-synthetically starting from the above protected kanamycin A derivative of the formula (I).

Thus, we have now found that the 3'- and 2"-hydroxyl groups of the protected kanamycin A derivative (I) can be imidazolylthiocarbonylated by reacting with 2 molar proportions or more of thiocarbonyl di-imidazole in an organic solvent to produce the corresponding bis-imidazolylthiocarbonylated product which can then be reacted with tri-butyltin hydride $(C_4H_9)_3SnH$ to remove preferentially the imidazolylthiocarbonyloxy group from the 3'-position of said bis-imidazolylthiocarbonylated product and thereby to give the corresponding 3'-deoxygenated product, and that this 3'-deoxygenated product can be subjected to successive steps for removal of the 2"-O-imidazolylthiocarbonyl group by treating with aqueous ammonia; for removal of the tosyl groups by treating with metal sodium in liquid ammonia; for fission of the 4',6'-cyclic carbamate ring by basic hydrolysis; and for concurrent removal of the 5,2'-O-isopropylidene group and 4",6"-O-cyclohexylidene group by acidic hydrolysis to afford the desired 3'-deoxykanamycin A. We have also found that the 2"-hydroxyl group of the protected kanamycin A derivative (I) can preferentially be acetylated for the protection of it by reacting with about 1 molar proportion of acetyl chloride in pyridine to give the corresponding 2"-O-acetylated product which can then be reacted with trifluoromethanesulfonic acid anhydride in pyridine to trifluoromethanesulfonylate the 3'-hydroxyl group, and that the 3'-O-trifluoromethanesulfonylated product so obtained can be subjected to successive steps for concurrent removal of the 3'-trifluoromethanesulfonyloxy group and the N-tosyl groups by treating with metal sodium in liquid ammonia; for removal from the resulting 3'-deoxygenated product of the 2"-O-acetyl group simultaneously with fission of the 4',6'-cyclic carbamate ring by basic hydrolysis; and for concurrent removal of the 5,2'-O-isopropylidene group and 4",6"-O-cyclohexylidene group by acidic hydrolysis to produce the desired 3'-deoxykanamycin A.

The principal object of this invention is to provide a new process for producing 3'-deoxykanamycin A semisynthetically from kanamycin A which is carried out in a facile way to give a favorable yield of the desired product.

Other objects of this invention will be clear from the following description.

According to a first aspect of this invention, therefore, there is provided a process for the production of 3'-deoxykanamycin A, which comprises the steps of:

(a) reacting a protected kanamycin A derivative of the formula

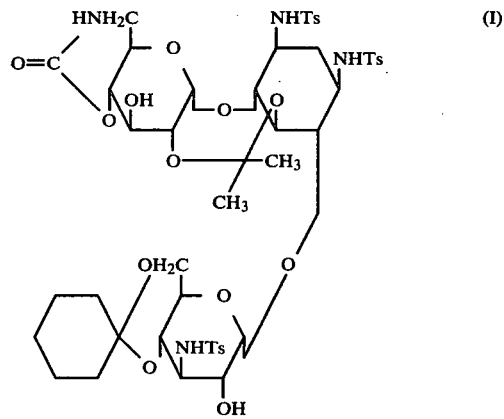

(I)

wherein Ts denotes tosyl group, with at least 2 molar proportions of thiocarbonyl di-imidazole in an organic solvent at a temperature of 40°–150° C. to effect the introduction of the imidazolylthiocarbonyl groups into 3'- and 2"-hydroxyl groups of the protected kanamycin A derivative (I), giving the corresponding, bis-imidazolylthiocarbonylated product, (b) removing preferentially the 3'-imidazolylthiocarbonyloxy group from the bis-imidazolylthiocarbonylated product by reacting with tri-butyltin hydride in an organic solvent at a temperature of 40°–150° C. to produce the 3'-deoxygenated product of the formula

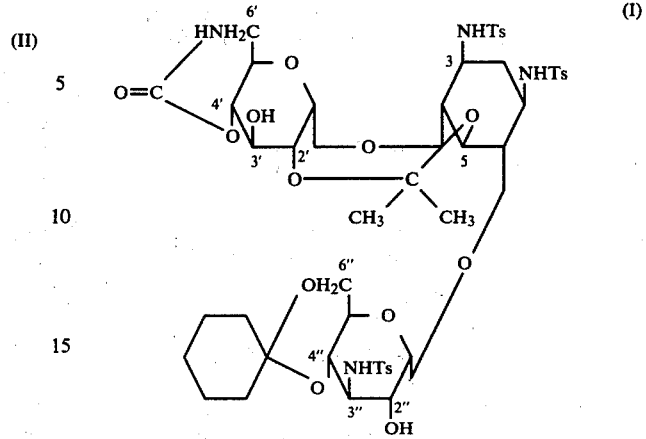

(I)

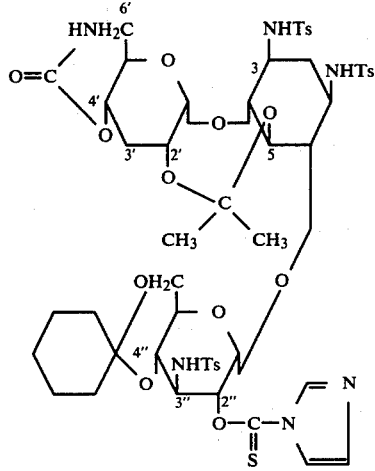

(II)

wherein Ts is as defined above, (c) removing the 2″-O-imidazolylthiocarbonyl group from the above 3′-deoxygenated product by reacting with aqueous ammonia, (d) removing the N-tosyl groups (Ts) by reacting with an alkali metal or alkaline earth metal in liquid ammonia in a known manner, (e) opening the 4′,6′-cyclic carbamate ring by basic hydrolysis in a known manner, and (f) removing concurrently the 5,2′-O-isopropylidene group and the 4″,6″-O-cyclohexylidene group by acidic hydrolysis in a known manner, to produce the desired 3′-deoxykanamycin A of the formula

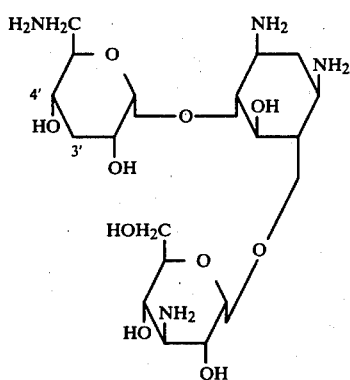

According to a second aspect of this invention, there is further provided a process for the production of 3′-deoxykanamycin A, which comprises the steps of:

(a) reacting a protected kanamycin A derivative of the formula wherein Ts denotes tosyl group, with 1–4 molar proportions of acetyl chloride in pyridine at a temperature of from minus 20° C. to ambient temperature to acetylate preferentially the 2″-hydroxyl group of the kanamycin A derivative (I), giving the corresponding, 2″-O-acetylated product, (b) reacting the 2″-O-acetylated product with trifluoromethanesulfonic acid anhydride in pyridine at a temperature of minus 20° C.–50° C. to trifluoromethanesulfonylate the 3′-hydroxyl group and to give the 3′-O-trifluoromethanesulfonylated product of the formula

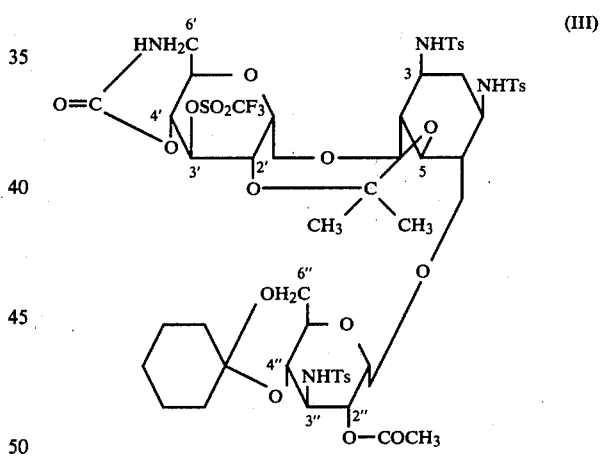

(III)

wherein Ts denotes tosyl group, (c) removing concurrently the 3′-trifluoromethanesulfonyloxy group and the N-tosyl groups from the 3′-O-trifluoromethanesulfonylated product (III) by reacting with an alkali metal or alkaline earth metal in liquid ammonia at a temperature of minus 80° C. to 0° C., to give the corresponding 3′-deoxygenated product, (d) hydrolyzing the 3′-deoxygenated product under alkaline conditions to remove the 2″-O-acetyl group therefrom and concurrently to open the 4′,6′-cyclic carbamate ring, and (e) removing concurrently the 5,2′-O-isopropylidene group and the 4″,6″-O-cyclohexylidene group by acidic hydrolysis to produce the desired 3′-deoxykanamycin A.

The procedures for carrying out the process of the first aspect invention are now described. In the first step of the present process, the protected kanamycin A derivative of the formula (I) as the starting material is reacted with thiocarbonyl di-imidazole of the formula

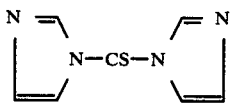

This reaction is effected in an organic solvent in which both the reagents are soluble, and particularly an organic solvent of the ether type and an organic solvent of Cellosolve type, for example, tetrahydrofuran and dioxane are suitable. The reaction is carried out at a temperature of 40°–150° C. and preferably of 50°–100° C. for a time of 6–24 hours, and the reaction may be made under pressure, if necessary. Thiocarbonyl di-imidazole is used in 2 molar proportion or more for 1 molar proportion of the starting compound (I), though it may be used in an exess. It is convenient to dissolve the starting compound (I) in an organic solvent such as tetrahydrofuran, admix the resultant solution with thiocarbonyl di-imidazole, and then heat the admixture so as to accomplish the reaction for introduction of an imidazolylthiocarbonyl group into both the 3'- and 2"-hydroxyl groups of the starting compound. The bis-imidazolylthiocarbonylated product so formed is represented by the formula (IV)

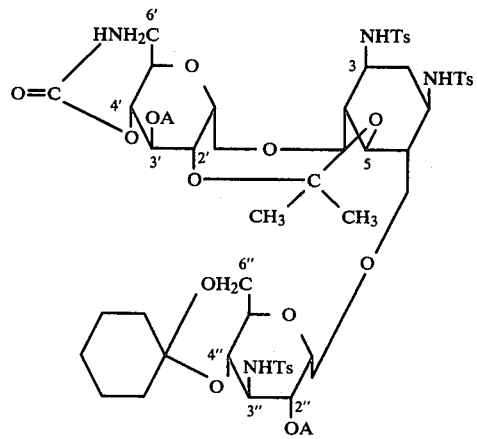

wherein Ts denotes tosyl group, and A denotes imidazolylthiocarbonyl group

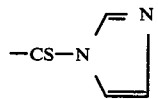

In the second step of the present process, the bisimidazolylthiocarbonylated product (IV) is reacted with tributyltin hydride under heating in an organic solvent in which both the reactants are soluble and which may be of the same kind as that employed in the first step of the present process. This reaction may be effected at a temperature of 40°–150° C. and preferably of 100°–120° C. for a time of 1–10 hours. Tributyltin hydride is preferably used in an amount of at least 2 mol. per 1 mol of the product (IV), and the reaction may be effected under pressure, if necessary. The reaction may conveniently be carried out in such a manner that the product (IV) is dissolved in an organic solvent such as tetrahydrofuran and the like and the resultant solution is admixed with tributyltin hydride, followed by heating the admixture. By this reaction, the 3'-position of the product (IV) is selectively reduced with removal of 3'-imidazolylthiocarbonyloxy group therefrom but without affecting the 2"-position. This procedure for the deoxygenation has been developed by Barton et al (D. H. R. Barton and S. W. McCombic; "J. Chem. Soc." Parkin I page 1574 (1975)), but we have confirmed experimentally that amongst the various reagents proposed by Barton et al, only the combined use of thiocarbonyl di-imidazole and tributyltin hydride is effective as the deoxygenating reagent for the kanamycin A derivative (I), and that the other reagents of Barton et al cannot be used effectively for the 3'-deoxygenation of the kanamycin A compound. Besides, according to the theory of Barton et al, it was expected that the 2"-hydroxyl group should be deoxygenated by removal of the 2"-imidazolylthiocarbonyloxy group. Contrary to this expectation, however, we have discovered that the 2"-imidazolylthiocarbonyloxy group is not removed and hence 2"-deoxygenation does not take place in the kanamycin A compound in the process of this invention. Accordingly, it is very unique that the desired 3'-deoxygenation is selectively achieved by the process of this invention.

In this way, the 3'-deoxy-2"-O-imidazolylthiocarbonyl derivative of the formula (II) is produced, and this product is then treated with aqueous ammonia in a subsequent, third step of the present process to effect the removal of the 2"-O-imidazolylthiocarbonyl group. In the further steps of the process, the remaining protective groups, namely the N-tosyl groups, the 4',6'-carbamate ring, the 4",6"-O-cyclohexylidene group and the 5,2'-O-isopropylidene group are removed successively by a deprotecting technique known for each of the protective groups which remain in each partially deprotected product, until the desired 3'-deoxykanamycin A is gained. The sequence in which the remaining various protective groups are removed may, in principle, be chosen optionally, but the above-mentioned sequence of removing the protective groups is convenient.

In the above-mentioned third step of the present process, the 3'-deoxy-2"-O-imidazolylthiocarbonyl product of the formula (II) may be treated with aqueous ammonia at a temperature of 0°–50° C. The aqueous ammonia may be used in the form of its mixture with an appropriate organic solvent such as tetrahydrofuran and ethanol, and the concentration of the ammonia in such mixture may be 5–20% by weight. Thus, the 2"-O-imidazolylthiocarbonyl group is removed.

In the further deprotecting steps of the present process, the N-tosyl groups present in the amino groups of the 3'-deoxykanamycin A derivative may be removed by treating with an alkali metal, especially metal sodium or an alkaline earth metal in liquid ammonia in a known manner eg., as described in U.S. Pat. No. 4,169,939. For use in the treatment in liquid ammonia, one or more of alkali metals selected from lithium, sodium and potassium, as well as alkaline earth metals selected from calcium, magnesium and barium, may be chosen. The reaction may be effected at a temperature of minus 80° C. to 0° C., for example, in a sealed tube or in a pressure vessel. The reaction time may suitably be 0.5 to 24 hours. The quantity of the alkali or alkaline earth metal used for this reaction may suitably be 10 to 100 mol. per mol. of the kanamycin A compound to be deprotected and may also be added at once or in small portions into the reaction mixture. After the reaction of removing the residual amino-protecting tosyl groups (Ts) is completed, the reaction mixture may be admixed with an amount of water, an alkanol or ammonium chloride to consume the remaining excessive quantity of the alkali metal or alkaline earth metal, followed by evaporating off the solvent (the liquid ammonia), dissolving the residual solid product in water and subjecting the resulting solution to a purification step, for example, a chromatographic process for purification purposes.

In a further deprotecting step of the present process, the fission of the 4',6'-carbamate ring may be effected by alkaline hydrolysis in a known a manner as described in the "Journal of Antibiotics" Vol. 25, No. 12, pp. 741-742 (1972). For example, the de-tosylated product obtained as above may be subjected to hydrolysis under alkaline conditions in an aqueous organic solvent such as aqueous dioxane containing an amount of an alkali metal carbonate such as sodium carbonate or barium hydroxide to open the 4',6'-carbamate ring of the kanamycin A compound. The hydrolysis may be effected at a temperature of 20° to 100° C. (see U.S. Pat. No. 4,125,706). As a consequence of the hydrolytic fission of the 4',6'-carbamate ring, the free 4'-hydroxyl group and free 6'-amino group are liberated.

The removal of the 4",6"-O-cyclohexylidene group and the 5,2'-O-isopropylidene group hydroxyl-protecting groups may be achieved simultaneously be acidic hydrolysis in a known manner, for example, using aqueous acetic acid such as aqueous solution containing 50-90% acetic acid. This acidic hydrolysis may be effected at a temperature of 50°-100° C. In accordance with the process of the invention in its first aspect, 3'-deoxykanamycin A may be obtained in an overall yield of about 15%, as calculated from the initial kanamycin A.

The procedures for carrying out the process of the invention in its second aspect are described below.

In the first step of the present process, the protected kanamycin A derivative of the formula (I) as the starting compound is reacted with at least 1 molar proportion, preferably 1.5-4 molar proportions of acetyl chloride in pyridine at a temperature below ambient temperature and preferably of 0° C. to minus 20° C. for a time 1-5 hours, when the 2"-hydroxyl group of the kanamycin A compound can be acetylated preferentially. This is a discovery firstly made by us. This selective 2"-O-acetylation does not take place if acetic anhydride is employed which has usually been employed for the acetylation of a hydroxyl group.

In the second step of the present process, the 2"-O-acetylated product obtained as above is reacted with trifluoromethanesulfonic acid anhydride in pyridine according to the method of the present inventors already reported (see Tsuchiya, Nakamura and Umezawa; "Tetrahydron Letters" 2805, (1975)). By this reaction, trifluoromethanesulfonyl group is introduced into the 3'-hydroxyl group to produce the 3'-O-trifluoromethanesulfonylated product of the formula (III). Trifluoromethanesulfonic acid anhydride may be used in an amount of 1.2-6 mol. per mol. of the kanamycin A compound. The 3'-O-trifluoromethanesulfonylation may be effected at a temperature of minus 20° C. to 50° C. for a time of 0.5-5 hours.

After the introduction of the 3'-O-trifluoromethanesulfonyl group, the 3'-trifluoromethanesulfonyloxy group is removed in a subsequent, third step of the present process by treating with an alkali metal or alkaline earth metal in liquid ammonia in the same manner as described hereinbefore in respect to the third step of the process of the invention in its first aspect, so that the desired 3'-deoxygenation can be achieved. Concurrently with the removal of the 3'-trifluoromethanesulfonyloxy group, the tosyl groups as the amino-protecting group can be removed, too. In this treatment in liquid ammonia, metal sodium is preferred. The reaction may be effected at a temperature of minus 80° C. to 0° C. for a time of 0.5-3 hours using 10 to 100 mol. of sodium metal per mol. of the kanamycin A compound. Noticeably, we have observed experimentally that when the 3'-hydroxyl group of the above-mentioned 2"-O-acetylated kanamycin A product has been sulfonylated by reacting with an alkyl-, aralkyl- or arylsulfonyl group other than the trifluoromethanesulfonyl group specifically employed in this invention, the 3'-sulfonyloxy group so obtained cannot be removed and hence 3'-deoxygenation cannot be achieved by treating with an alkali or alkaline earth metal, particularly with sodium metal in liquid amonia, whereupon only the free 3'-hydroxyl group can be regenerated.

Subsequently to the above step for the 3'-deoxygenation and concurrent removal of the N-tosyl groups, the resulting 3'-deoxykanamycin A product is further subjected to the deprotecting steps for removal of the residual protective groups, that is, the 2"-O-acetyl group, the 4',6'-carbamate ring, the 4",6"-O-cyclohexylidene group and the 5,2'-O-isopropylidene group by a known deprotecting technique. The removal of the 2"-O-acetyl group may be achieved by alkaline hydrolysis. The fission of the 4',6'-carbamate ring and the removal of the cyclohexylidene and isopropylidene groups can be achieved by the same procedures as described hereinbefore with respect to the process of the invention in its first aspect. In accordance with the invention in its second aspect, 3'-deoxykanamycin A can be obtained in an overall yield of about 12%, as calculated from the initial kanamycin A.

Preparation of the protected kanamycin A derivative of the formula (I) which is used as the starting compound in the processes of this invention is now described and illustrated later with reference to Example 3.

Kanamycin A is used as the initial material and its 6'-amino group is protected by alkoxycarbonylating, aryloxycarbonylating or aralkyloxycarbonylating this amino group selectively in a known manner to introduce the amino-protecting alkoxycarbonyl, aryloxycarbonyl or aralkyloxycarbonyl group. As the 6'-group is more reactive than the other amino groups of kanamycin A, the amino-protecting group of an alkoxycarbonyl, aryloxycarbonyl or aralkyloxycarbonyl type may be introduced preferentially into the 6'-amino group, for example, by reacting 1 molar proportion of kanamycin A (free base) in water with 0.5 to 3 molar proportion of a chloroformate of the formula:

BCl wherein B represents an alkoxycarbonyl group of 2 to 6 carbon atoms, an aryloxycarbonyl group such as phenyloxycarbonyl or an aralkyloxycarbonyl group such as benzyloxycarbonyl, at a temperature of 0° to 10° C. according to the method of Kawaguchi et al as described in the "Journal of Antibiotics" 25, 695-708 (1972) or U.S. Pat. No. 3,781,268, for example. It is then convenient to prepare, for example, 6'-N-benzyloxycarbonylkanamycin A according to the method of Example 1 of U.S. Pat. No. 3,925,353. The 6'-N-alkoxycarbonyl-, 6'-N-aryloxycarbonyl- or 6'-N-aralkyloxycarbonyl-kanamycin A so prepared may be converted into the corresponding 1,3,3''-tri-N-tosyl-kanamycin A by tosylating it in an organic solvent such as aqueous dioxane.

The preparation of the 1,3,3''-tri-N-tosyl-kanamycin A derivative may preferably be conducted, e.g., in the following way. The 6'-N-protected kanamycin A is reacted with a substantially stoichiometric quantity (i.e. 3 molar proportion or more) of tosyl chloride in an organic solvent such as dioxane or aqueous dioxane at a temperature of 30° to 50° C. in the presence of an amount of alkali such as sodium carbonate to give the 6'-N-protected-1,3,3''-tri-N-tosyl-kanamycin A. The 1,3,3''-tri-N-tosylated kanamycin A so obtained is then reacted with a cyclohexylidenylating agent, 1,1-dimethoxycyclohexane at a temperature of e.g. 10° to 80° C. to protect the 4''- and 6''-hydroxyl group with the divalent hydroxyl-protecting group in a known manner as described in Japanese Patent Publication No. 7595/75 or U.S. Pat. No. 3,929,762. In this way, the 4''- and 6''-hydroxyl groups are blocked simultaneously by a cyclohexylidene group.

The 4'',6''-O-protected kanamycin A derivative prepared as above is dissolved in an appropriate organic solvent such as dimethylformamide and then reacted with a basic reagent, particularly an alkali metal hydride such as sodium hydride similarly to a known method as described in the "Journal of Antibiotics" Vol. 25, No. 12, 741–742 (1972) or U.S. Pat. No. 3,925,354 or 4,125,706 to give the corresponding 4',6'-cyclic carbamate. If the stage of forming the 4',6'-cyclic carbamate is omitted and then if only tetra-N-tosylkanamycin A is immediately reacted with 2,2-dimethoxypropane or 1,1-dimethoxycyclohexane, the 2'-hydroxyl group of the kanamycin A compound cannot be blocked selectively. Accordingly, it has been devised to take a course in which the 4',6'-cyclic carbamate is first formed and then the 2'- and 5-hydroxyl groups are blocked by 5,2'-O-isopropylidenation.

The 4',6'-cyclic carbamate derivative prepared as above is then dissolved in a suitable inert organic solvent such as dichloroethane and is further reacted with 2,2-dimethoxypropane under anhydrous conditions in the presence of an acidic catalyst such as toluenesulfonic acid or sulfuric acid to protect the 5- and 2'-hydroxyl groups of the kanamycin A compound with the divalent hydroxyl-protecting group, isopropylidene group. In this reaction, there are formed the 5,2'-O-protected derivative of the formula (I) and a corresponding 2',3'-O-protected derivative in substantially equal amounts. The former compound may be separated from the latter by utilizing the difference in their solubility in a proper organic solvent such as chloroform. For this purpose, a chromatographic separation is also possible.

This invention is illustrated with reference to the following Examples to which is not limited this invention. Example 1 is illustrative of the first aspect of this invention, and Example 2 is illustrative of the second aspect of this invention.

EXAMPLE 1

(1) Production of 4'-O:6'-N-carbonyl-4'',6''-O-cyclohexylidene-5,2'-O-isopropylidene-3',2''-O-bis (imidazolylthiocarbonyl)-1,3,3''-tri-N-tosylkanamycin A 4'-O:6'-N-Carbonyl-4'',6''-O-cyclohexylidene-5,2'-O-isopropylidene-1,3,3''-tri-N-tosylkanamycin A (1.0 g) (see Example 3 given later) was dissolved in 15 ml of tetrahydrofuran, and to the resulting solution was added thiocarbonyl di-imidazole (970 mg). The mixture was heated at 55° C. for 12 hours, and the reaction solution was concentrated to a smaller volume and admixed with a volume of ethyl ether. The precipitate as deposited was removed by filtration and well washed with ethyl ether to give 1.2 g of the titled compound as a colorless solid. Yield 99%.

$[\alpha]_D^{23} + 130°$ (c=0.2, acetone)
Elemental Analysis: Found: C 51.96, H.5.26, N 8.37, S 11.92%; Calcd. for $C_{57}H_{68}N_8O_{18}S_5$: C 52.12, H 5.22, N 8.53, S 12.20%

(2) Production of 4'-O:6'-N-carbonyl-4'',6''-O-cyclohexylidene-3'-deoxy-5,2'-O-isopropylidene-2''-O-imidazolylthiocarbonyl-1,3,3''-tri-N-tosylkanamycin A The product (580 mg) obtained in the above procedure (1) was dissolved in 14 ml of tetrahydrofuran, followed by addition of 1.16 g of tributyltin hydride to the resultant solution. The admixture obtained was heated at 110° C. for 3 hours in a sealed tube of glass. The reaction solution was concentrated to a smaller volume and admixed with a volume of ethyl ether. The precipitate as deposited was removed by filtration and well washed with ethyl ether to afford 480 mg of the titled compound as a solid. Yield 90%.

$[\alpha]_D^{25} + 65°$ (c=0.3, acetone)
Elemantal Analysis: Found: C 53.81, H 5.76, N 6.81, S 10.91%; Calcd. for $C_{53}H_{66}N_6O_{17}S_4$: C 53.61, H 5.60, N 7.08, S 10.80%

(3) Production of 4'-O:6'-N-carbonyl-4'',6''-O-cyclohexylidene-3'-deoxy-5,2'-O-isopropylidene-1,3,3''-tri-N-tosylkanamycin A The substance (285 mg) obtained in the above procedure (2) was dissolved in 1 ml of conc. aqueous ammonia-tetrahydrofuran-ethanol (4:1:2.5 by volume), and the resulting solution was allowed to stand at ambient temperature for 2 hours to effect the hydrolytic removal of the 2''-O-imidazolylthiocarbonyl group. The reaction solution was then concentrated to a smaller volume and subsequently admixed with a volume of water. The precipitate as deposited was removed by filtration and washed with water to afford 252 mg of the title compound as a solid. Yield 97%.

$[\alpha]_D^{25} + 34°$ (c=0.5, acetone)
Elemental Analysis:
Found: C 54.37, H 6.17, N 5.42, S 9.03%; Calcd. for $C_{49}H_{64}N_4O_{17}S_3$: C 54.63, H 5.99, N 5.20, S 8.93%

(4) Production of 3'-deoxykanamycin A

The substance (148 mg) obtained in the above procedure (3) was dissolved in 10 ml of liquid ammonia at −50° C., to which was then added 100 mg of sodium metal. The admixture was agitated for 1 hour 20 minutes at −50° C. to effect the removal of the tosyl groups. To the admixture was further added a volume of tetrahydrofuran containing 5% water, until the blue color of the admixture disappeared and the residual sodium metal was consumed. The reaction mixture was concentrated by evaporation of liquid ammonia and then admixed with a volume of water, followed by heating at 85° C. for 1 hour, during which fission of the 4',6'-carbamate ring remaining in the de-tosylated product was accomplished. The resulting reaction solution in water was passed through a column of 5 g. of a strongly acidic cation-exchange resin, Dowex 50 W×2 ($SO_3H^+$ form) (a product of Dow Chemical Co., U.S.A.) for adsorption of the desired product. The resin was washed with water and then eluted with 1 N aqueous ammonia, and the eluate was concentrated to dryness to give a solid. This solid was dissolved in 80% aqueous acetic acid and then heated at 80° C. for 1 hour 20 minutes to effect the simultaneous removal of the 4",6"-O-cyclohexylidene group and the 5,2'-O-isopropylidene group. The reaction solution was concentrated under reduced pressure to give a crude solid of 3'-deoxykanamycin A.

This solid was dissolved in 1 ml of water, and the aqueous solution was passed through a column of a gel-filtration agent, CM-Sephadex C-25 ($NH_4^+$ form) (a product of Pharmacia Fine Chemical Co., Sweden). The Sephadex column was washed with water and then chromatographed gradiently using 0.03 N→0.15 N aqueous ammonia as the eluent. Such fractions of the eluate which contained the desired 3'-deoxykanamycin A solely were combined together and concentrated to dryness to give 44 mg of 3'-deoxykanamycin A monocarbonate as a colorless solid. Yield 61%.

$[\alpha]_D^{25} + 119°$ (c=0.5, water)

Elemental Analysis:

Found: C 43.00, H 7.49, N 10.60%; Calcd. for $C_{18}H_{36}N_4O_{10} \cdot H_2CO_3$: C 43.01, H 7.22, N 10.56%

The product obtained was coincident with an authentic sample of 3'-deoxykanamycin A with respect to the physicochemical properties and antibacterial activity.

EXAMPLE 2

(1) Production of 2"-O-acetyl-4"-O:6'-N-carbonyl-4",6"-O-cyclohexylidene-5,2'-O-isopropylidene-1,3,3"-tri-N-tosylkanamycin A 4'-O:6'-N-Carbonyl-4"6"-O-cyclohexylidene-5,2'-O-isopropylidene-1,3,3"-tri-N-tosylkanamycin A (100 mg) was dissolved in 4.0 ml of pyridine, and the resultant solution was admixed with 0.018 ml of acetyl chloride at −17° C. The admixture obtained was allowed to stand at −17° C. for 1 hour 20 minutes to effect preferential 2"-O-acetylation. The reaction solution was then mixed with 0.04 ml of water, concentrated to a smaller volume and then admixed with a large volume of 5% aqueous sodium hydrogen carbonate. The precipitate as deposited was removed by filtration and washed with water to afford 103 mg of the titled compound as a solid. Yield 99%.

$[\alpha]_D^{25} + 40°$ (c=0.4, acetone)

Elemental Analysis:

Found: C 53.68, H 5.83, N 4.69, S 8.19%; Calcd. for $C_{51}H_{66}N_4O_{19}S_3$: C 53.96, H 5.86, N 4.94, S 8.47%

(2) Production of 2"-O-acetyl-4'-O:6'-N-carbonyl-4",6"-O-cyclohexylidene-5,2'-O-isopropylidene-1,3,3"-tri-N-tosyl-3'-O-trifluoromethanesulfonylkanamycin A The substance (206 mg) obtained in the above procedure (1) was dissolved in 2.0 ml of pyridine, and the resultant solution was admixed with 0.079 ml of trifluoromethanesulfonic acid anhydride at −18° C., followed by agitation at −18° C. for 20 minutes. The mixture was then allowed to stand at +3° C. for 20 minutes and further at ambient temperature for 1 hour 25 minutes to effect the 3'-O-trifluoromethanesulfonylation. The reaction mixture, after addition of a solution of 50 mg of sodium carbonate in 1.5 ml of water thereto, was concentrated to a smaller volume, and the concentrated solution was admixed with a large volume of 5% aqueous sodium hydrogen carbonate. The precipitate as deposited was collected by filtration and washed with water to give 116 mg of the title compound as a solid. Yield 97%.

$[\alpha]_D^{25} + 48°$ (c=0.4, acetone)

Elemental Analysis: Found: C 48.95, H 5.38, N 4.12, S 9.95, F 4.13%; Calcd. for $C_{52}H_{65}N_4O_{21}S_4F_3$: C 49.28, H 5.17, N 4.42, S 10.12, F 4.50%

(3) Production of 3'-deoxykanamycin A

The substance (62.5 mg) obtained in the above procedure (2) was dissolved in 5 ml of liquid ammonia at −50° C., to which was then added 80 mg of sodium metal. The whole mixture was agitated for 1 hour 10 minutes at −50° C. to effect the removal of the 3'-trifluoromethanesulfonyloxy group concurrently with the removal of the tosyl groups. To the mixture was further added a volume of tetrahydrofuran containing 5% water until the blue color of the admixture disappeared and the residual sodium metal was consumed. The reaction mixture was concentrated to a smaller volume by evaporation of liquid ammonia, and the concentrated solution was admixed with a volume of water, followed by heating at 85° C. for 1 hour during which removal of the 2"-O-acetyl group and fission of the 4',6'-carbamate took place. The reaction solution in water was passed through a column of the cation-exchange resin, Dowex 50 W×2 ($SO_3H^+$ form) (a product of Dow Chemical Co., U.S.A.) for adsorption of the desired product. The resin column, after washing with water, was eluted with 1 N aqueous ammonia, and the eluate was concentrated to dryness to give a solid comprising 4",6"-O-cyclohexylidene-5,2'-O-isopropylidene-3'-deoxykanamycin A. This solid was dissolved in 80% aqueous acetic acid, followed by heating at 80° C. for 2 hours to effect the concurrent removal of the cyclohexylidene and isopropylidene groups. The reaction solution was concentrated under reduced pressure to afford a crude solid of 3'-deoxykanamycin A.

This solid was dissolved in 1 ml of water, and the aqueous solution obtained was passed through a column of a gel-filtration agent, CM-Sephadex C-25 ($NH_4^+$ form) (a product of Pharmacia Fine Chemical Co., Sweden). The Sephadex column was washed with water and then chromatographed gradiently using 0.03 N→0.15 N aqueous ammonia as the eluent. Such fractions of the eluate which contained the desired product solely were combined together and concentrated to dryness to give 11.5 mg of 3'-deoxykanamycin A monocarbonate as a colorless solid. Yield 44%.

This product was coincident with an authentic sample of 3'-deoxykanamycin A with respect to physicochemical properties and antibacterial activity.

EXAMPLE 3

This example shows the preparation of the starting compound of the formula (I) employed in this invention.

(1) Preparation of 6'-N-benzyloxycarbonyl-1,3,3''-tri-N-tosylkanamycin A

6'-N-Benzyloxycarbonylkanamycin A (free base) (1.79 g) (see the aforesaid "Journal of Antibiotics" Vol. 25, 695–708 (1972)) and anhydrous sodium carbonate (1.1 g) were dissolved in 50 ml of a mixture of water and dioxane (1:3 by volume), and to the resulting solution was added 2.0 g of p-toluene-sulfonyl chloride under stirring. The admixture obtained continued to be stirred at ambient temperature overnight (for the tri-N-tosylation) and then concentrated to a smaller volume. The concentrated solution was admixed with a volume of water, and the precipitate as deposited was removed by filtration, washed with ethyl ether and dried to give the above titled product as a solid. Yield 3.14 g (98%).

$[\alpha]_D^{25} + 10°$ (c=0.4, acetone).

Elemental Analysis:

Found: C 52.10, H 5.56, N 5.12, S 8.68%; Calcd. for $C_{47}H_{60}N_4O_{19}S$: C 52.21, H 5.59, N 5.18, S 8.90%

(2) Preparation of 6'-N-benzyloxycarbonyl-4'',6''-O-cyclohexylidene-1,3,3''-tri-N-tosylkanamycin A The substance (1.29 g) obtained in the above procedure (1) was taken up into 4 ml of dimethylformamide, and the resulting solution was admixed with 45 mg of toluene-sulfonic acid and 0.86 ml of 1,1-dimethoxycyclohexane. The admixture obtained was allowed to stand at ambient temperature for 6 hours (for the 4'',6''-O-cyclohexylidenation). The reaction mixture was then poured into a large volume of a solution of sodium hydrogen carbonate in water, and the precipitate so deposited was removed by centrifugation, well washed with water and then dried. Yield 1.35 g (98%).

$[\alpha]_D^{25} + 0°$ (c=0.5, acetone).

Elemental Analysis:

Found: C 54.89, H 6.10, N 4.63, S 8.52%; Calcd. for $C_{53}H_{68}N_4O_{19}S_3$: C 54.81, H 5.90, N 4.82, S 8.28%

(3) Preparation of 4'',6''-O-cyclohexylidene-1,3,3''-tri-N-tosyl-4'-0:6'-N-carbonyl-kanamycin A

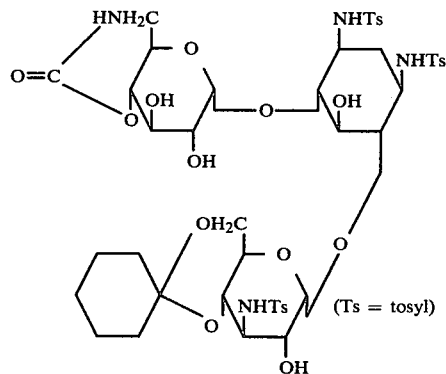

The substance (911 mg) obtained in the above procedure (2) was dissolved in 18 ml of dimethylformamide, and to the resultant solution was added 337 mg of 50% sodium hydride in oil. The admixture was agitated overnight at ambient temperature and then admixed with 3.5 ml of 4 N aqueous acetic acid and further with 50 ml of toluene. The whole admixture was distilled to remove the solvents, and the thick syrup so obtained was admixed with a large volume of water. The precipitate deposited was collected by filtration, washed with ethyl ether and dried to give a colorless solid comprising the above titled compound. Yield 685 mg (85%).

(4) 4'',6''-O-cyclohexylidene-4'-0:6'-N-carbonyl-5,2'-O-isopropylidene-1,3,3''-tri-N-tosylkanamycin A

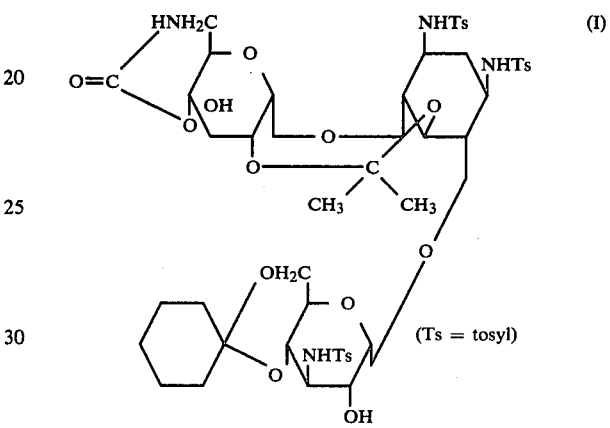

The substance (100 mg) obtained in the above procedure (3) was suspended in a mixture of 4 ml of dichloromethane and 2.5 ml of tetrahydrofuran, and to the resulting suspension was added 2 ml of 2,2-dimethoxypropane. The admixture obtained was further mixed with 6 ml of a solution of 0.035 N hydrogen chloride in dichloromethane, followed by heating for 17 minutes under reflux (for the 5,2'-O-isopropylidenation). This reaction was conducted in a reactor vessel fitted with a reflux column at the top of the reactor vessel where a column containing 5 ml of "Molecular Sieves 5A" (a product of zeolite produced by Union Carbide Co., U.S.A.) was interposed between the bottom of the reflux column and an outlet opening in the top of the reactor vessel in such a way that the vapour distilled from the reaction solution present in the vessel could arise through a side-armed tube which was connected directly between the reaction vessel and the bottom of the reflux column, so that the condensed vapour containing methanol falling down in the reflux column could then pass via the column of molecular sieves and so that only methanol could be removed by adsorption by the molecular sieves. Thus, the condensed solvent freed from methanol could again come back into the reaction vessel. If the above reaction solution was heated simply under reflux without removing the methanol vapour by means of said molecular sieve column, the undesired 2',3'-O-isopropylidene derivative was by-produced in a very much higher proportion than the desired 5,2'-O-isopropylidene derivative, so that the latter product desired was formed in a very poor yield and could not be recovered in a substantial yield.

The reaction mixture from the above reaction was cooled by ice-cooling and then poured into a large volume of a mixture of dioxane and 1 N aqueous ammonia, and the resulting admixture was concentrated. The concentrated solution obtained was diluted with a volume of ethyl ether to precipitate a colorless solid. This solid was collected by filtration, washed with water and dried to give 85 mg of a solid. This solid was taken up into 3 ml of chloroform and the resultant solution was chromatographed in a column of 5 ml of silica gel developed with chloroform-ethanol (10:1 by volume) as the eluent for purification purposes. The effluent running out of the silica gel column was concentrated to dryness in vacuo to give 61 mg of a solid. This solid was again taken up into 5 ml of chloroform, and the solution was heated. As the heating proceeded, the undesired 2′,3′-O-isopropylidene derivative became deposited. The whole solution was allowed to stand at ambient temperature overnight, followed by filtration. The filtrate so obtained was concentrated to dryness, giving 32 mg of the above titled desired product.

$[\alpha]_D^{25} + 20°$ (c=0.5, acetone).

What we claim is:

1. A process for the production of 3′-deoxykanamycin A, which comprises the steps of:

(a) reacting a protected kanamycin A derivative of the formula

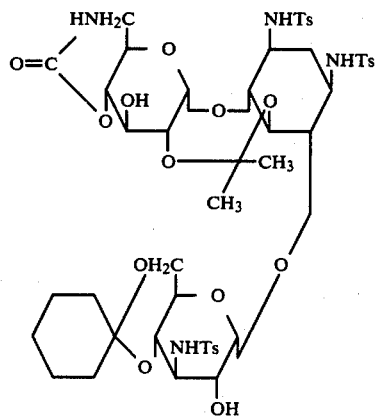

wherein Ts denotes a tosyl group, with at least 2 molar proportions of thiocarbonyl di-imidazole in an organic solvent at a temperature of 40°–150° C. to effect the introduction of the imidazolylthiocarbonyl groups into the 3′ and 2″-hydroxyl groups of the protected kanamycin A derivative (I), giving the corresponding, bis-imidazolylthiocarbonylated product, (b) removing the 3′-imidazolyl-thiocarbonyloxy group from the bis-imidazolylthiocarbonylated product by reacting with tri-butyltin hydride in an organic solvent at a temperature of 40°–150° C. to produce the 3′-deoxygenated product of the formula

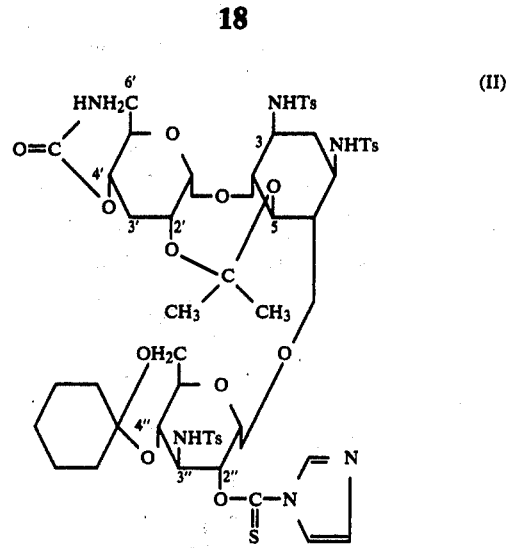

wherein Ts is as defined above, (c) removing the 2″-O-imidazolylthiocarbonyl group from the above 3′-deoxygenated product by reacting with aqueous ammonia, (d) removing the N-tosyl groups by reacting with an alkali metal or alkaline earth metal in liquid ammonia, (e) opening the 4′,6′-cyclic carbamate ring by basic hydrolysis, and (f) removing concurrently the 5,2′-O-isopropylidene group and the 4″,6″-O-cyclohexylidene group by acidic hydrolysis, to produce the desired 3′-deoxykanamycin A.

2. A process for the production of 3′-deoxykanamycin A, which comprises the steps of:

(a) reacting a protected kanamycin A derivative of the formula

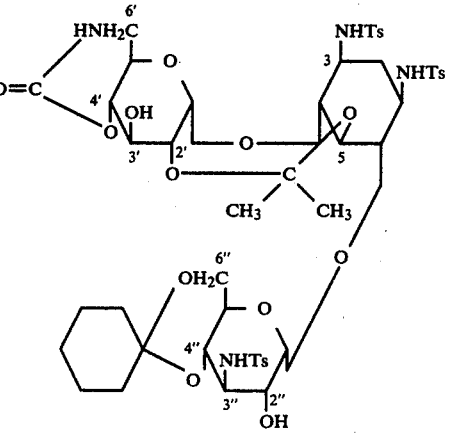

wherein Ts denotes a tosyl group, with 1–4 molar proportions of acetyl chloride in pyridine at a temperature of from minus 20° C. to ambient temperature to acetylate the 2″-hydroxyl group of the kanamycin A derivative (I), giving the corresponding, 2″-O-acetylated product, (b) reacting the 2″-O-acetylated product with trifluoromethanesulfonic acid anhydride in pyridine at a temperature of minus 20° C.–50° C. to trifluoromethane-sulfonylate the 3′-hydroxyl group and to give the 3'-O-trifluoromethanesulfonylated product of the formula

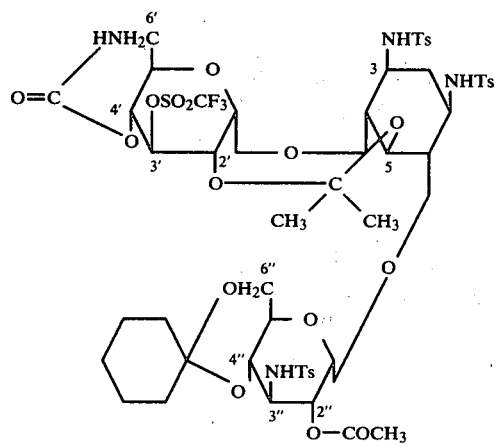

wherein Ts denotes a tosyl group,
(c) removing concurrently the 3'-trifluoromethanesulfonyloxy group and the N-tosyl groups from the 3'-O-trifluoromethanesulfonylated product (III) by reacting with an alkali metal or alkaline earth metal in liquid ammonia at a temperature of minus 80° C. to 0° C., to give the corresponding 3'-deoxygenated product,
(d) hydrolyzing the 3'-deoxygenated product under alkaline conditions to remove the 2"-O-acetyl group therefrom and concurrently to open the 4',6'-cyclic carbamate ring, and
(e) removing concurrently the 5,2'-O-isopropylidene group and the 4",6"-O-cyclohexylidene group by acidic hydrolysis to produce the desired 3'-deoxykanamycin A.

3. 4'-O:6'-N-Carbonyl-4",6"-O-cyclohexylidene-5,2'-O-isopropylidene-3',2"-O-bis(imidazolylthiocarbonyl)-1,3,3"-tri-N-tosylkanamycin A.

4. 2"-O-Acetyl-4'-O:6'-N-carbonyl-4",6"-O-cyclohexylidene-5,2'-O-isopropylidene-1,3,3"-tri-N-tosylkanamycin A.

5. 2"-O-Acetyl-4'-O:6'-N-carbonyl-4",6"-O-cyclohexylidene-5,2'-O-isopropylidene-1,3,3"-tri-N-tosyl-3'-O-trifluoromethanesulfonylkanamycin A.

* * * * *